(12) United States Patent
Coll

(10) Patent No.: US 6,331,076 B1
(45) Date of Patent: Dec. 18, 2001

(54) SOLDER PASTE WITH A TIME-TEMPERATURE INDICATOR

(75) Inventor: Brian M. Coll, Salthill (IE)

(73) Assignee: Manufacturers' Services Ltd., Concord, MA (US)

( * ) Notice: Subject to any disclaimer, the term of this patent is extended or adjusted under 35 U.S.C. 154(b) by 0 days.

(21) Appl. No.: 09/183,680

(22) Filed: Oct. 30, 1998

(51) Int. Cl.[7] .................................................. G01K 11/00

(52) U.S. Cl. ...................... 374/102; 374/162; 116/207; 116/216; 283/81; 283/114; 53/507

(58) Field of Search ..................................... 374/161, 162, 374/102, 160, 150; 116/207, 216; 53/507; 283/81, 114

(56) References Cited

U.S. PATENT DOCUMENTS

| 3,999,946 |   | 12/1976 | Patel et al. ............................. 23/253 |
|---|---|---|---|
| 4,154,107 | * | 5/1979 | Giezen et al. ....................... 374/102 |
| 4,189,399 |   | 2/1980 | Patel ..................................... 252/408 |
| 4,208,186 | * | 6/1980 | Patel ..................................... 116/207 |
| 4,228,126 |   | 10/1980 | Patel et al. ............................. 422/56 |
| 4,278,561 |   | 7/1981 | Yee ...................................... 252/408 |
| 4,339,240 |   | 7/1982 | Patel ..................................... 23/230 R |
| 4,389,217 |   | 6/1983 | Baughman et al. .................... 436/2 |
| 4,432,656 | * | 2/1984 | Allmendinger ..................... 116/216 |
| 4,812,053 |   | 3/1989 | Bhattacharjee ....................... 374/102 |
| 4,892,677 | * | 1/1990 | Preziosi et al. ...................... 374/162 |
| 5,045,283 | * | 9/1991 | Patel ..................................... 116/207 |
| 5,053,339 | * | 10/1991 | Patel ..................................... 116/207 |
| 5,057,434 | * | 10/1991 | Prusik et al. ......................... 116/207 |
| 5,254,473 |   | 10/1993 | Patel ..................................... 436/1 |
| 5,667,303 |   | 9/1997 | Arens et al. .......................... 374/102 |
| 5,709,472 | * | 1/1998 | Prusik et al. ......................... 374/150 |
| 5,997,927 | * | 12/1999 | Gics ..................................... 116/207 |

FOREIGN PATENT DOCUMENTS 0 054 831   12/1981   (EP) .
0 264 939   10/1987   (EP) .

OTHER PUBLICATIONS

Chris Bastecki, et al., "What Do Time, Temperature, Humidity and Production Pauses Have in Common?. . . " (1997). Oct. 15, 1997.
Kester, "Shipping and Storage," Solder Paste Data Sheet Supplement (visited Aug. 27, 1996) <http://www.metcal.com/kester/pstsuppl.html>.
Kester, Kester Solderpaste Handling and Storage Recommendations (visited Aug. 6, 1998) <http://www.metcal.com/kester/pststore.html>.
Kester, Product Data Sheet: OA/Water Soluble Solderpaste Formula R596 (1995). Aug. 7, 1995.
Kester, Product Data Sheet: Water Washable Solder Paste Stenciling Formula WS–850 (1996). Apr. 30, 1990.
Qualitek®, Product Data Sheet: Delta® 792 Solder Paste Water Soluble (1996). Mar. 29, 1996.
Lifelines Technology, Fresh–Check® Product Literature. No Date.
Cox Technologies, Vitsab Information/Site Map (revised Nov. 5, 1998) <http://www.cx–en.com/moreinfo.htm>.
Cox Technologies, Vitsab Quick Summary (revised Nov. 5, 1998) <http://www.cx–en.com/tags.htm>.
Cox Technologies, Vitsab Shrink Savings (revised Nov. 5, 1998) <http://www.cx–en.com/shrink.htm>.
Cox Technologies, Vitsab Consumer Perspectives (revised Nov. 5, 1998) <http://www.cx–en.com/consumer.htm>.

(List continued on next page.)

Primary Examiner—Diego Gutierrez
Assistant Examiner—Jeanne-Marguerite Goodwin
(74) Attorney, Agent, or Firm—Hamilton, Brook, Smith & Reynolds, P.C.

(57) ABSTRACT

A solder paste product includes solder paste in a container with a time-temperature indicator positioned to measure the solder paste's cumulative exposure to heat.

21 Claims, 2 Drawing Sheets

OTHER PUBLICATIONS

Cox Technologies, Vitsab Product Type List (revised Nov. 5, 1998) >http://www.cx–en.com/TTI–code.htm>.

Cox Technologies, Vitsab Technical Information (revised Nov. 5, 1998) <http://www.cx–en.com/vitsabtech.htm>.

Cox Technologies, Vitsab Technical Course (revised Nov. 5, 1998) <http://www.cx–en.com/vit–course.htm>.

Cox Technologies, Vitsab Color Development (revised Nov. 5, 1998) <http://www.cx–en.com/vitcolor.htm>.

Cox Technologies, Independent Certification (revised Nov. 5, 1998) <http://www.cx–en.com/taoukis.htm>.

Cox Technologies, Vitsab FAQ (revised Nov. 5,1998) <http://www.cx–en.com/vitsabfaq.htm>.

Cox Technologies, Calculating the Arrhenius Equation (revised Nov. 5, 1998) <http://www.cx–en.com/calc.htm>.

Cox Technologies, Vitsab Product Type List (revised Nov. 5, 1998) <http://www.cx–en.com/TTI–code.htm>.

VITSAB®, Bibliography (revised May 9, 1997) <http://www.vitsab.com/vitbibl.htm>.

VITSAB®, Salmon Study—Otwell (revised Apr. 27, 1998) <http://www.vitsab.com/salmon.htm>.

VITSAB®, Lettuce Study—Singh (revised Jul. 13, 1998) <http://vitsab.com/singh–lettuce.htm>.

VITSAB®, Inexpensive Time Temperature Labels (revised Jun. 16, 1998) <http://www.vitsab.com/>.

VITSAB®, More Information—Website Contents (revised Apr. 27, 1998) <http://www.vitsab.com/moreinfo.htm>.

VITSAB®, Quick Summary (revised Sep. 29, 1998) <http://www.vitsab.com/tags.htm>.

VITSAB®, Quick Facts–FAQ (revised Jun. 16, 1998) <http://www.vitsab.com/vitsab–qk.htm>.

VITSAB®, Technical Course (revised May 25, 1997) <http://www.vitsab.com/vit–course.htm>.

* cited by examiner

SOLDER PASTE WITH A TIME-TEMPERATURE INDICATOR

BACKGROUND OF THE INVENTION

Solder paste is typically maintained in a refrigerated state to preserve the integrity of its composition and to thereby prolong its useful shelf life. Refrigeration is needed because when solder paste is subjected to prolonged heat exposure, it typically suffers from chemical deterioration and physical suspension problems. Moreover, when solder paste deteriorates due to heat exposure, it often fails to meet expected performance standards as a bonding agent.

Consequently, the storage and handling of solder paste is an area which has come under increasing scrutiny in the drive to reduce variation in surface mount technology (SMT) manufacturing processes. Typically, a container of solder paste is stamped with a six-month date signaling the expiration of the solder paste's useful shelf life (i.e., the duration of time during which the freshness or integrity of the paste can be ensured, given proper handling of the paste). The duration of six months is based on a preestablished thermal forecast for the solder paste over the course of its life with a margin of safety provided.

The solder paste's actual shelf life, however, is dependent on the nature of temperature excursions that the paste actually experiences from the time it is manufactured to the time it is reflowed on a board. To preserve the quality of the paste, these temperature variations need to be monitored and controlled. Temperature variations are typically monitored by logging, over time, the temperature of the refrigerated environment where the solder paste is maintained.

SUMMARY OF THE INVENTION

By its very nature, the traditional process for monitoring the thermal history of solder paste is unreliable because it fails to consider that the paste may see excess temperatures during transport and during unexpected contingencies, such as a temporary loss of power to a refrigerator. It also lacks precision because it monitors the temperature of the environment where the solder paste containers are stored rather than the actual temperature of each solder paste container. The faithful execution of the traditional monitoring process is further complicated in that the production, transport and storage stages in the life of solder paste are filled with discontinuities, such as when a container is transferred from a shipping container to a refrigerator.

Moreover, the objective of the traditional monitoring process is modest. It seeks only to ensure that the quality of the solder paste can be preserved for the duration of the baseline six-month shelf life in accordance with the expiration date stamped on the container.

A solder paste product of this invention overcomes these limitations and offers greatly enhanced capabilities regarding the monitoring of the solder paste's useful shelf life. The solder paste product includes a container filled with solder paste and a time-temperature indicator positioned to measure the solder paste's cumulative exposure to heat.

In accordance with a method of this invention, the time-temperature indicator is attached to the container.

The time-temperature indicator is preferably a label including an indicator composition, e.g., a diacetylene monomer, that changes color as a function of heat exposure. At any given time, the color of the indicator composition is a function of its cumulative exposure to heat. The higher the temperature, the faster the indicator composition will change colors. If the temperature is dropped, the rate at which the indicator changes color will slow. The label may also include a colored reference marker, designed, in conjunction with the indicator composition, to provide a color match between the reference marker and the indicator composition as the solder paste approaches the exhaustion of its useful shelf life. In accordance with one aspect of the invention, the indicator composition is such that if the label is maintained at a fixed temperature, the logarithm of the time that will elapse before the color of the indicator composition is darker than that of the reference marker is an approximately linear function of the temperature.

The time-temperature indicator of this invention offers the advantages of providing the user with a reliable and easy-to-read indication of the condition of solder paste within a container. If a time-temperature label is attached to a jar of solder paste before it leaves the manufacturer, the label will show the temperature excursions to which the jar has been subjected through the shipping, storage and handling process. In contrast to conventional practice, the method of this invention establishes an expiration date based not on off-site speculation as to the thermal conditions that the solder paste will experience over the course of its life, but rather, on those temperatures to which the solder paste is actually subjected. As a result, a consumer will know that a batch of solder paste, which has been well refrigerated throughout its life, can be safely used beyond the traditional six-month expiration date. Conversely, the label on another batch, which was subject to a failure in the refrigeration chain, may indicate to the user that the useful shelf life of the paste has been reduced and, accordingly, that the paste should soon be used. This knowledge is likely both to enhance the proper utilization of "fresh" solder paste and to increase consumer confidence levels in product quality.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The features and other details of the method of the invention will now be more particularly described with reference to the accompanying drawings and pointed out in the claims. Numbers that appear in more than one figure represent the same item. It will be understood that the particular embodiments of the invention are shown by way of illustration and not as limitations of the invention. The principal features of this invention can be employed in various embodiments without departing from the scope of the invention.

Figure 1:
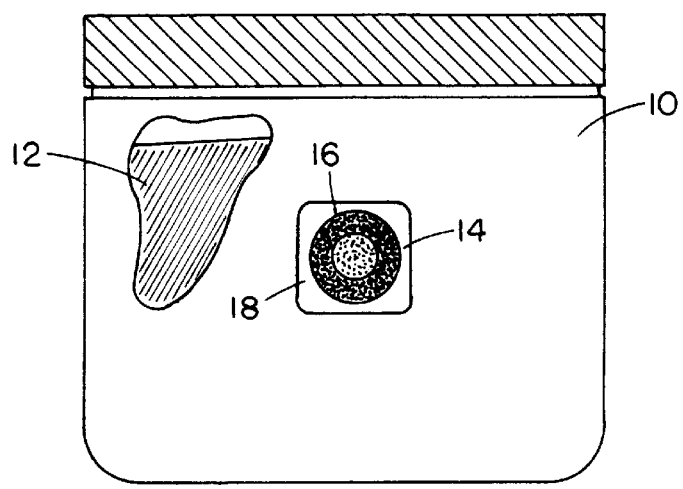
FIG. 1 is an illustration of a solder paste container with a time-temperature label and a cut-away view revealing the solder paste within the container.

As illustrated in FIG. 1, a solder paste product of this invention includes a container 10 filled with solder paste 12. Attached to the container 10 is a time-temperature label 14 for measuring the solder paste's cumulative exposure to heat.

The solder paste 12 typically includes a powdered solder suspended in a flux along with a suitable vehicle and plasticizers. Typical alloys used as powdered solder are Sn63Pb37 and Sn62Pb36Ag02. The flux includes a base and active ingredients. The base gives the paste body, and the active ingredients supply the flux with chemical strength, apart from that of the base material. Finally, the vehicle and plasticizer are provided to enhance the consistency of the flux.

In a reflow process during soldering, the solder paste 12 is heated to cause the solder and flux to react. Although it is generally necessary for the flux and solder to react during reflow, any reactions between the two components before reflow should be strictly limited because premature reaction between the solder and the flux can irreversibly render the paste 12 unsuitable for soldering.

The rate of reaction between the powdered solder and flux is temperature dependent, whereby the solder paste 12 will react much more rapidly at higher temperatures. However, even the relatively slow reaction rate of the paste 12 at low temperatures necessitates that the quality of refrigerated solder paste be monitored over time. The time-temperature profile of the useful shelf life of solder paste over a range of temperatures can be fit to a plot of expiration dates for solder paste stored at different temperatures. The end of a paste's useful shelf life, or the expiration date of the paste, is characterized by a deleterious change in the slump, tackiness and/or viscosity of the paste. The expiration dates can be established by experiment and/or observation, or they can be extracted from widely-published industry standards as are commonly available on manufacturers' data sheets. For example, in accordance with industry standards, solder paste for use in fabricating consumer electronics is expected to have a useful shelf life of at least 6 months when stored at 5° C., and that same consumer-electronics grade solder paste, is expected to have a useful shelf life of at least 2 weeks if stored at ambient temperature (i.e., 20° C.). Further still, the solder paste has been observed to have a useful shelf life of 3 days when stored at 30° C. Finally, the solder has been observed to have a useful shelf life of 1 day when paste stored at 40° C. Additional points on the time-temperature shelf-life profile can be determined and refined by empirical methods.

The precise expiration values vary from paste to paste, and the industry-standard expiration values that are generally relied upon are often conservatively calculated to provide a margin of safety. In actuality, at least one brand of consumer-electronics grade solder paste has been observed to have a useful shelf-life of 1 year at 5° C. and 4 weeks at 20° C. Nevertheless, the useful shelf life of a typical consumer-electronics grade solder paste as a function of prolonged temperature exposure can be safely assumed to approximately match the values plotted in the graph of FIG. 3, which tracks the time-temperature response profile of Fresh-Check® Indicator Type C 1 (available from LifeLines). This indicator is described in greater detail, below.

Suitable containers 10 for storing the solder paste 12 include a 500 g jar; a 600, 1000 or 1400 g cartridge; or a 35 or 100 g syringe. The container 10 typically should provide a vapor-proof seal to prevent the solder paste 12 from oxidizing.

The time-temperature label 14 perceptibly changes color as a function of temperature. The color of the label 14 at any given time is a product of the integral of the temperature to which the label 14 has been exposed over time. A preferred embodiment of a time-temperature label 14 used in this invention is a human-readable, self-adhesive strip, wherein the indicator composition is an inner circle 16 of color-changing chemistry surrounded by a ring 18 providing a reference color. When the color of the inner circle 16 is darker than the reference ring 18, the end of the useful shelf life of both the solder paste 12 and the label 14 is signaled.

Figures 2A, 2B, 2C, 2D:
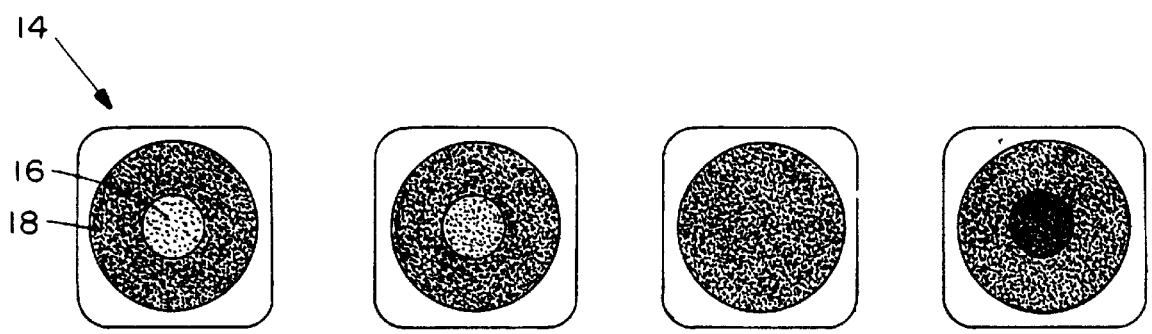
FIGS. 2A–D provide illustrations of a time-temperature label through a progression of freshness levels.

The color progression of a time-temperature label 14 is illustrated in FIGS. 2A–D. A freshly applied label 14 is illustrated in FIG. 2A. Note that the inner circle 16 is much lighter than the reference marker provided by the ring 18. The label 14 in FIG. 2B exhibits some exposure to heat since the circle 16 is darker than that of the label 14 in FIG. 2A. Nevertheless, the label 14 still denotes that the solder paste 12 is fresh because it remains lighter than the reference ring 18. The label 14 in FIG. 2C evidences further heat exposure, as the color of the circle 16 nearly matches that of the reference ring 18. At this point, the solder paste 12 should be used immediately. Finally, the label 14 of FIG. 2D is expired as indicated by the fact that the circle 16 is now darker than the reference ring 18. At this point, the quality of the solder paste 12 can no longer be guaranteed.

To produce a label 14 that generates a color match at the close of the useful shelf life of any given solder paste, the chemical composition of the inner circle 16, or indicator composition, can be adjusted. Further, the label 14 can be subjected to a carefully-controlled preliminary heating procedure designed to shorten the length of time before a color match is produced. By using processes, such as these, to alter the chemistry of the indicator, the life of the label 14 can be matched to the life of the paste 12. To facilitate this match, an Arrhenious relationship can be used to describe the dependence of both the solder paste 12 and the label 14 on time and temperature.

In a preferred embodiment, the inner circle 16 includes diacetylene monomers of a composition described, for example, in U.S. Pat. Nos. 3,999,946; 4,189,399; 4,228,126; 4,339,240; and 4,389,217; each of which is incorporated herein by reference in its entirety. Labels 14 of this type are available from Lifelines Technology, Inc. (Morris Plains, N.J., U.S.A.). Although the monomers may initially be colorless, the indicator compositions develop color as a result of solid-state polymerization of the diacetylene monomers. The solid-state polymerization is a heat-driven process. Accordingly, the rate at which the circle 16 darkens increases with increasing temperature.

Figure 3:
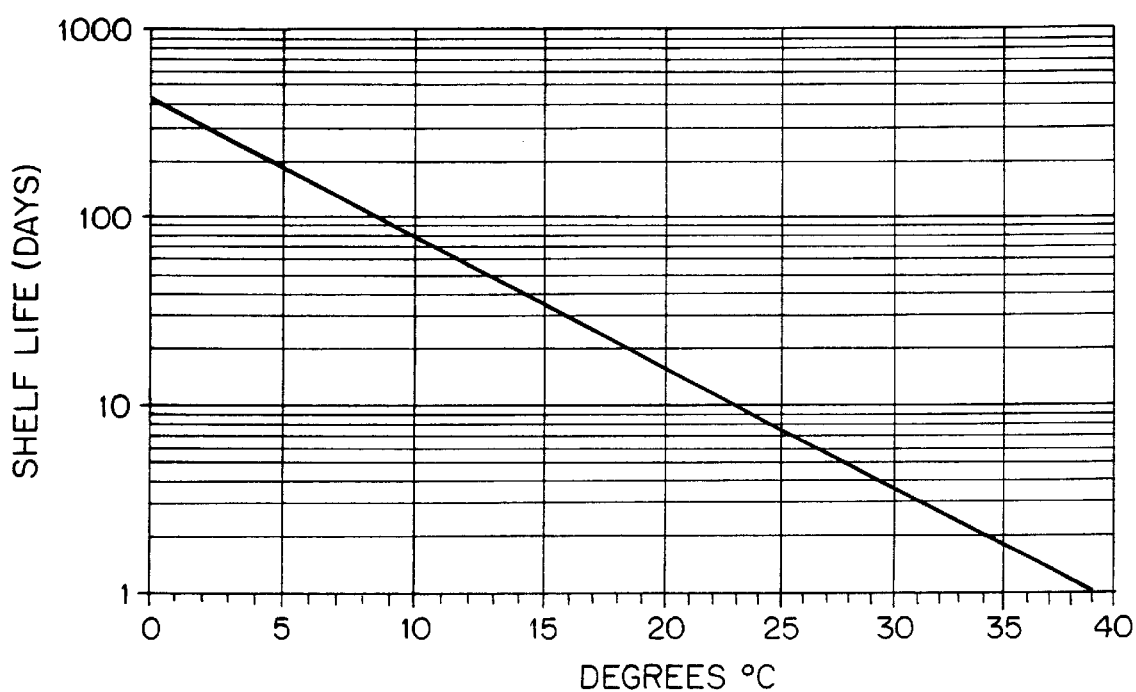
FIG. 3 is a graph illustrating, as a function of fixed temperature, the date on which a time-temperature label will indicate the end of the solder paste's useful shelf life. In this example, the paste is shown to have a useful shelf life of 6 months when stored at 5° C.

LifeLines Technology, Inc. produces a series of time-temperature labels 14 with response times covering a range of time-temperature profiles. Many of these labels have previously been employed to monitor the freshness of perishable foods and pharmaceuticals. Among these labels 14 are specific models that can be matched to the time-temperature characteristics of solder paste 12. The time-temperature profile of one such label 14, Fresh-Check® Indicator Type C1 (available from LifeLines), is illustrated in FIG. 3. The profile of the label's life, or response time (i.e., the time elapsed before the label's inner circle 16 becomes darker than the outer reference ring 18) provides a close match to the duration of the solder paste's useful shelf life at each of the temperatures. Depending on the composition of other solder pastes, different label models may be needed to produce more accurate matches of the time-temperature profile.

Solder paste manufacturers are presently attempting to extend the useful shelf life of solder paste by developing pastes having less sensitivity to heat. As new pastes with longer shelf lives are developed, the chemistry of the inner circle can be changed to provide an indicator that is correspondingly less sensitive to heat and that will, therefore, change colors more slowly.

After the labels 14 are manufactured, they are stored in a freezer at approximately −30° C. At this temperature, Fresh-Check® labels 14 can be maintained for more than six months without any measurable color change. Further, the labels 14 will age only slightly at normal freezer temperatures.

As the solder paste 12 is processed and packaged, labels 14 are withdrawn from the freezer and applied to the solder paste containers 10. Once attached to the container 10, the labels 14 can be visually inspected throughout the delivery and storage process to ensure that the quality of the solder paste 12 has not deteriorated. If the inner circle 16 is darker than the outer reference ring 18, this indicates to the supplier, distributer, retailer or consumer that the solder paste 12 has reached the end of its useful shelf life. Moreover, as the inner circle progressively darkens, it also serves as an indicator to the user of the useful shelf life remaining for the paste.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A solder paste product comprising:
   a container;
   solder paste contained within the container; and
   a time-temperature indicator positioned on the container to measure the solder paste's cumulative exposure to temperature, the indicator having a time-temperature profile corresponding to a time-temperature profile of the solder paste.

2. The solder paste product of claim 1, wherein the indicator includes an indicator composition, the indicator composition having a color that is a function of the indicator's cumulative exposure to beat.

3. The solder paste product of claim 2, wherein the indicator composition changes color at a rate that increases with increasing temperature.

4. The solder paste product of claim 2, wherein the indicator further includes a colored reference marker.

5. The solder paste product of claim 4, wherein the indicator composition is formulated to reach a color darker than the color of the reference marker when the solder paste is at the end of its useful shelf life.

6. The solder paste product of claim 4, wherein the indicator composition, when maintained at a fixed temperature, will become darker than the reference marker after a duration of time, and wherein the logarithm of the duration of time is a linear function of the fixed temperature.

7. The solder paste product of claim 4, wherein the indicator composition includes a diacetylene monomer.

8. A method of making a solder paste product comprising the steps of:
   attaching a time-temperature indicator to a container of solder paste, the indicator having a time-temperature profile corresponding to a time-temperature profile of the solder paste; and
   measuring the cumulative exposure of the solder paste to temperature.

9. The method of claim 8, wherein the time-temperature indicator includes an indicator composition that changes color as a function of its exposure to heat.

10. The method of claim 9, wherein the indicator composition changes color at a rate that increases with increasing temperature.

11. The method of claim 10, wherein the time-temperature indicator further includes a colored reference marker.

12. The method of claim 11, wherein the indicator composition is formulated to be darker than the color of the reference marker when the solder paste is at the end of its useful shelf life.

13. The method of claim 12, wherein the indicator composition, when maintained at a fixed temperature, will become darker than the reference marker after a duration of time, and wherein the logarithm of the duration of time is a linear function of the fixed temperature.

14. The method of claim 8, wherein the indicator composition includes a diacetylene monomer.

15. The method of claim 8, further comprising the step of monitoring the time-temperature indicator to evaluate the status of the solder paste in terms of its useful shelf life.

16. A method for monitoring the temperature of solder paste comprising:
   providing solder paste in a container, the solder paste having a time-temperature profile;
   providing a time-temperature indicator having a time-temperature profile corresponding to the time-temperature profile of the solder paste;
   attaching the time-temperature indicator to the container; and
   monitoring changes in the time-temperature indicator, the cumulative changes in the indicator corresponding to changes in the useful life of the solder paste caused by temperature.

17. The method of claim 16 further comprising transporting the solder paste.

18. The method of claim 16 further comprising providing an indicator composition on the time-temperature indicator that changes color with exposure to heat.

19. The method of claim 18 further comprising allowing the time-temperature indicator to change color as a function of its exposure to heat.

20. The method of claim 18 further comprising allowing the time-temperature indicator to change color of a rate that increases with increasing temperature.

21. The method of claim 18 further comprising comparing the color of the time-temperature indicator to a colored reference marker to determine the useful life of the solder paste.

* * * * *